United States Patent [19]

Borrett et al.

[11] Patent Number: 5,618,948

[45] Date of Patent: Apr. 8, 1997

[54] PROCESS FOR PREPARING AN ENANTIOMER OF A CARBAZOLE DERIVATIVE

[75] Inventors: Gary T. Borrett, Stansted; John Kitteringham, Hertford; Roderick A. Porter, Ashwell; Mark R. Shipton, Bishop's Stortford; Mythily Vimal, Edmonton; Rodney C. Young, Oxford, all of England

[73] Assignee: SmithKline Beecham p.l.c., England

[21] Appl. No.: 451,846

[22] Filed: May 26, 1995

Related U.S. Application Data

[63] Continuation-in-part of PCT/EP93/03627, Dec. 16, 1993.

[51] Int. Cl.⁶ .................................................. C07D 209/88
[52] U.S. Cl. ................................................................ 548/448
[58] Field of Search .............................................. 548/448

[56] References Cited

U.S. PATENT DOCUMENTS 4,257,952  3/1981  Mooradian ............................. 548/448

FOREIGN PATENT DOCUMENTS

WO93/00086  1/1993  WIPO .

OTHER PUBLICATIONS

Hacksell et al., "Chirality in drug research and design", *Trends in Biotechnology*, vol. 11, pp. 73–74 (1993).

Ariens, "Nonchiral homochiral and composite chiral drugs", *Trends in Pharmacological Sciences*, vol. 14, pp. 68–75 (1993).

*Primary Examiner*—Robert W. Ramsuer
*Attorney, Agent, or Firm*—Nora Stein-Fernandez; William T. King; Edward T. Lentz

[57] ABSTRACT

A (+) or (−) enantiomer of a compound of formula (I) wherein $R^4$ is methyl or ethyl, or a salt, solvate or hydrate thereof, processes for preparing said compounds and pharmaceutical compositions containing them. Compounds of formula (+) are $5\text{-HT}_1$-like agonists.

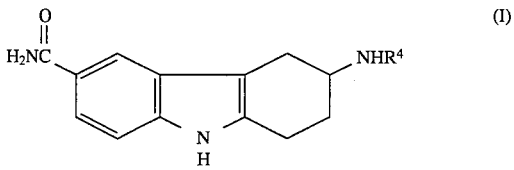

1 Claim, No Drawings

PROCESS FOR PREPARING AN ENANTIOMER OF A CARBAZOLE DERIVATIVE

This is a continuation of PCT application Ser. No. PCT/EP93/03627, filed Dec. 16, 1993, which claimed priority from GB 9226530.5, filed on Dec. 21, 1992.

The present invention relates to certain tetrahydrocarbazole derivatives, in particular their enantiomeric forms, processes for preparing them, pharmaceutical compositions containing them and their use in therapy, in particular the treatment of migraine.

International Patent Application WO93/00086 describes compounds of the formula:

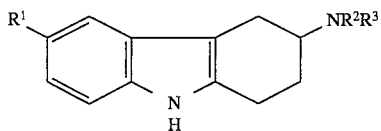

and salts thereof for use in the treatment of conditions wherein a 5-HT$_1$-like agonist is indicated, in particular migraine.

In the above compounds $R^1$ represents hydrogen, halogen trifluoromethyl, nitro, hydroxy, $C_{1-6}$alkyl, $C_{1-6}$alkoxy, aryl$C_{1-6}$alkoxy, —$CO_2R^4$, —$(CH_2)_nCN$, —$(CH_2)_nCONR^5R^6$, —$(CH_2)_nSO_2R^5R^6$, $C_{1-6}$alkanoylamino$(CH_2)_n$, or $C_{1-6}$alkylsulphonylamino$(CH_2)_n$; $R^4$ represents hydrogen, $C_{1-6}$alkyl or aryl$C_{1-6}$alkyl; $R^5$ and $R^6$ each independently represent hydrogen, or $C_{1-6}$alkyl, or $R^5$ and $R^6$ together with the nitrogen atom to which they are attached form a ring: n represents 0, 1 or 2; and $R^2$ and $R^3$ each independently represent hydrogen, $C_{1-6}$alkyl or benzyl or together with the nitrogen atom to which they are attached form a pyrrolidino, piperidino or hexahydroazepino ring. The carbon atom to which the group $NR^2R^3$ is attached (i.e. at position 3 of the tetrahydrocarbazole ring) is an asymmetric carbon atom and hence the compounds exist as optically active enantiomers.

WO93/00086 describes inter alia the preparation of the above compounds wherein $R^1$ is —C(O)NH$_2$, one of $R^2$ and $R^3$ is hydrogen and the other is methyl or ethyl, viz:
6-carboxamido-3-N-methylamino-1,2,3,4-tetrahydrocarbazole (as the hydrochloride salt) and
6-carboxamido-3-N-ethylamino-1,2,3,4-tetrahydrocarbazole (as the oxalate salt). Both compounds were obtained only as mixtures of enantiomers.

We have now isolated the individual isomers of the above compounds. Thus, in a first aspect the present invention provides the (+) and (−) enantiomers of a compound of formula (I):

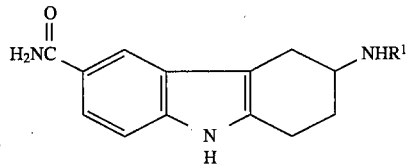

Formula (I)

wherein $R^1$ is methyl or ethyl, or a salt thereof.

In accordance with convention the (+) and (−) designations indicate the direction of rotation of plane-polarised light by the compounds. The prefix (+) indicates that the isomer is dextrorotatory (also designated d) and the prefix (−) indicates the levorotatory isomer (also designated l). The R and S designations denote the absolute configuration as determined by X-ray crystallography.

The individual compounds of formula (I) provided by the invention may be named as:
R-(+)-6-carboxamido-3-N-methylamino-1,2,3,4-tetrahydrocarbazole; (compound A)
S-(−)-6-carboxamido-3-N-methylamino-1,2,3,4-tetrahydrocarbazole; (compound B)
R-(+)-6-carboxamido-3-N-ethylamino-1,2,3,4-tetrahydrocarbazole; (compound C)
S-(−)-6-carboxamido-3-N-ethylamino-1,2,3,4-tetrahydrocarbazole. (compound D)

Salts, solvates and hydrates of the above named compounds are also within the scope of the present invention.

It will be appreciated that for use in medicine a physiologically acceptable salt should be employed. Suitable physiologically acceptable salts will be apparent to those skilled in the art and include for example acid addition salts such as those formed with inorganic acids e.g. hydrochloric, hydrobromic, sulphuric or phosphoric acids and organic acids e.g. succinic, tartaric, malonic, citric, maleic, acetic, fumaric or methanesulphonic acid. Other non-physiologically acceptable salts e.g. oxalates may be used for example in the isolation of enantiomers of formula (I), and are included within the scope of this invention. Also included within the scope of the invention are solvates and hydrates of enantiomers of formula (I) and their salts.

Acids which have more than one carboxyl group e.g. succinic, tartaric, malonic or citric acids may correspondingly react with more than one molecule of an enantiomer (I), for example succinic acid may react with either one or two molecules of (1) to form either a 1:1 salt (succinate) or a 2:1 salt (hemi-succinate). All such salt forms are encompassed by the present invention; in general the 1:1 salt form is preferred.

Specific salts according to the present invention include:
(+)-6-carboxamido-3-N-methylamino-1,2,3,4-tetrahydrocarbazole L (+)-tartrate salt (1:1),
(+)-6-carboxamido-3-N-methylamino-1,2,3,4-tetrahydrocarbazole D (−)-tartrate salt (1:1),
(+)-6-carboxamido-3-N-methylamino-1,2,3,4-tetrahydrocarbazole hemisuccinate (2:1),
(+)-6-carboxamido-3-N-methylamino-1,2,3,4-tetrahydrocarbazole methanesulphonate,
(+)-6-carboxamido-3-N-methylamino-1,2,3,4-tetrahydrocarbazole succinate (1:1),
(+)-6-carboxamido-3-N-methylamino-1,2,3,4-tetrahydrocarbazole hydrochloride,
(+)-6-carboxamido-3-N-methylamino-1,2,3,4-tetrahydrocarbazole hydrobromide,
(+)-6-carboxamido-3-N-ethylamino-1,2,3,4-tetrahydrocarbazole succinate (1:1),
(+)-6-carboxamido-3-N-ethylamino-1,2,3,4-tetrahydrocarbazole hydrochloride, and
(+)-6-carboxamido-3-N-methylamino-1,2,3,4-tetrahydrocarbazole camphorsulphonate.

It will be appreciated that an enantiomer according to the present invention for example a (+)- enantiomer, will be substantially free from the corresponding (−) enantiomer, and vice versa. Preferably, a specific enantiomer of the invention will contain less than 10%, e.g. less than 5% and advantageously less than 1% e.g. less than 0.5% of its opposite enantiomer.

In vitro testing (rabbit basilar artery) indicates that for both the methyl and ethyl derivatives of formula (I) the (+) enantiomer is more active than the corresponding (−) enantiomer. The above-named (+)-enantiomers are therefore preferred compounds of the invention.

Enantiomers of formula (I) may be prepared by standard methods, for example:

(a) Separation of an enantiomeric mixture of a compound of formula (I) or a derivative thereof by chromatography e.g. on a chiral HPLC column.

(b) Separation of diastereoisomers of a chiral derivative (e.g. a chiral salt) of a compound of formula (I) e.g. by crystallisation, or by chromatography.

(c) Alkylation of a (+) or (−) enantiomer of 3-amino-6-carboxamido-1,2,3,4-tetrahydrocarbazole or a salt thereof, followed if necessary or desired by converting a derivative of compound (I) so obtained into a compound of formula (I) itself or a different derivative thereof e.g by removal of any N-protecting group or facilitating group, conversion of a salt into the free base, and/or salt formation.

Separation according to process (a) is generally facilitated by first introducing a readily removable group into the alkylamino moiety of the compound of formula (I). Suitable removable facilitating groups include those commonly used as N-protecting groups e.g. an alkoxycarbonyl group such as t-butyloxycarbonyl or an aralkoxycarbonyl group such as benzyloxycarbonyl, which groups may be introduced by reaction with for example a di-alkyl-dicarbonate such as di-t-butyl-dicarbonate or a chloroformate such as benzylchloroformate. The resulting enantiomeric mixture can be applied to a chiral HPLC column and fractions containing the individual isomers collected. A facilitating group may be removed by standard methods such as acid hydrolysis or catalytic hydrogenation.

A chiral derivative according to process (b) is a derivative containing at least two chiral centres, such that an enantiomeric mixture of a compound (I) is converted into a pair of diastereoisomers. Such derivatives include chiral salts wherein the anion contains a chiral centre and derivatives of formula (I) in which the alkylamino moiety is substituted by a group containing a chiral centre.

A chiral salt may be prepared for example by reaction of an enantiomeric mixture, such as a 1:1 racemate, of a compound (1) with an optically active acid such as (1S)-(+)-camphorsulphonic acid, d-tartaric acid, l-malic acid, l-mandelic acid, l-gulonic acid, 2,3:4,6-di-O-isopropylidene-2-keto-L-gulonic acid or R-2-pyrrolidone-5-carboxylic acid (also known as D-pyroglutamic acid) to give two diastereoisomeric salts which may be separated e.g. by crystallisation. The free base form of the desired enantiomer may be obtained by neutralisation with a base such as sodium hydroxide or an ion exchange resin. Preferred optically active acids for use in this process include (1S)-(+)-camphorsulphonic acid and especially R-2-pyrrolidone-5-carboxylic acid.

Alternatively, an optically active reagent such as R-α-methylbenzyloxysuccinimidate may be reacted with an enantiomeric mixture of formula (I), to give a mixture of diastereoisomers which can be separated by chromatography, followed by hydrogenolysis to give the desired enantiomer of formula (I).

A chiral derivative may also be prepared by employing a chiral auxiliary at an earlier stage in the synthesis as described hereinafter. This may advantageously result in a mixture enriched with one diastereoisomer of a compound (I), and most preferably a single diastereoisomer, thus providing a stereoselective synthesis of an enantiomer according to the invention.

Alkylation of an enantiomer of 3-amino-6-carboxamido-1,2,3,4-tetrahydrocarbazole according to process (c) may be carried out by standard methods well known in the art. For example alkylation may be achieved indirectly by formation of a group which can be reduced to the desired alkylamino function (reductive alkylation). Thus for example the 3-amino compound can be reacted with an appropriate aldehyde or ketone e.g. formaldehyde, acetaldehyde or acetone, in the presence of a suitable reducing agent such as an alkali metal borohydride or cyanoborohydride e.g. sodium cyanoborohydride. Alternatively formylation may be effected using p-nitrophenol formate in aqueous tetrahydrofuran, using similar reducing conditions. Preferably, the 3-amino compound is first reacted with benzaldehyde, also in the presence of a reducing agent such as a cyanoborohydride, to form 3-N-benzylamino-6-carboxamido-1,2,3,4-tetrahydrocarbazole, prior to introduction of the methyl or ethyl group. The benzyl group may subsequently be cleaved by standard methods such as catalytic hydrogenation.

In a further alkylation method, an N-methyl substituent may be introduced by formation of a 3-isothiocyanato derivative e.g. by reaction of the 3-amino compound with carbon disulphide and dicyclohexylcarbodiimide; followed by reduction for example with a borohydride.

It will be appreciated by those skilled in the art that other standard means of alkylation may also be employed.

The starting compounds for use in the above processes may be prepared by methods known in the art for the preparation of tetrahydrocarbazoles, such as the methods described in International Application WO93/00086. Thus for example an enantiomeric mixture of formula (I) may be prepared by reductive alkylation of the corresponding 3-amino compound, as described for process (c) above.

An enantiomeric mixture of formula (I) may also be prepared by reaction of 4-carboxamido-phenylhydrazine, or a salt thereof e.g. the hydrochloride, with 4-(methyl or ethyl)-aminocyclohexanone. In a particular embodiment of this method a protected derivative of the 4-alkylaminocyclohexanone is advantageously employed, e.g. a ketal of formula (II):

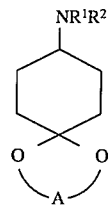

Formula (II)

wherein $R^1$ is as defined for formula (I), $R^2$ is hydrogen or an N-protecting group and A is an alkylene moiety, such as ethylene or neopentylene (—$CH_2C(CH_3)_2CH_2$—).

Compounds of formula (II) may themselves be prepared from a protected 1,4-cyclohexane-dione of formula (III):

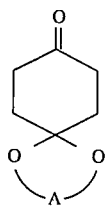

Formula (III)

by reaction with the appropriate alkylamine compound. This reaction may be effected in a suitable solvent, for example a hydrocarbon such as benzene or toluene in the presence of titanium tetrachloride or suitable molecular sieves e.g. 4Å molecular sieves, to give the corresponding iminoketal derivative which may then be converted to an alkylamino compound of formula (II) by catalytic hydrogenation using for example palladium on carbon. Alternatively the reaction may be effected in a solvent such as an alcohol e.g. ethanol and the mixture hydrogenated directly, using e.g. palladium on charcoal, to give a compound of formula (II).

The alkylamino group in the resulting compound of formula (II) may if desired be protected using standard methods. Suitable N-protecting groups are well-known in the art and include for example acyl groups such as acetyl, trifluoroacetyl, or benzoyl; an alkyl- or aralkyloxycarbonyl group such as methoxycarbonyl, t-butoxycarbonyl, benzyloxycarbonyl or phthaloyl; and aralkyl groups such as benzyl, diphenylmethyl or triphenylmethyl. The protecting groups should be easily removable at the end of the reaction sequence. N-deprotection may be effected by conventional methods, for example an alkoxycarbonyl group such as t-butoxycarbonyl may be cleaved by hydrolysis and an aralkyloxycarbonyl group such as benzyloxycarbonyl or an aralkyl group such as benzyl may be cleaved by hydrogenolysis.

Cyclisation with 4-carboxamidophenylhydrazine or a salt thereof is preferably carried out with a ketal of formula (II); however if desired the ketal may be converted to the corresponding ketone prior to this reaction.

Yet a further method for preparing an enantiomeric mixture of formula (I) comprises reacting a compound of formula (IV):

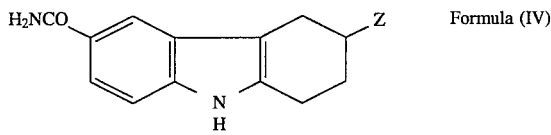

Formula (IV)

wherein Z is a leaving group, such as a halogen atom or a sulphonyloxy (e.g. p-toluenesulphonyloxy or methanesulphonyloxy) group with an amine $H_2NR^1$ or a derivative thereof. Said derivative may optionally contain a chiral centre, as in for example R-α-methylbenzylamine, resulting in a diastereoisomeric mixture of the corresponding derivative of formula (I). The diastereoisomers may be separated by chromatography, followed by hydrogenolysis to give the desired enantiomer of formula (I).

An enantiomeric mixture of 3-amino-6-carboxamido-1,2,3,4-tetrahydrocarbazole may be prepared in an analogous manner to formula (I), using 4-aminocyclohexanone, optionally protected as a ketal derivative, or an N-protected (e.g. phthalimido) derivative thereof. The enantiomers of 3-amino-6-carboxamido-1,2,3,4-tetrahydrocarbazole may be resolved by chiral HPLC as described for process (a) above, using a derivative such as of 3-t-butyloxycarbonylamino-6-carboxamido-1,2,3,4-tetrahydrocarbazole; or by formation of a chiral salt of the 3-amino compound in a similar manner to process (b) above, using for example 2,3-4,6-O-isopropylidene-2-keto-L-gulonic acid, followed by selective crystallisation. Such methods are described in International Application WO93/00086.

Enantiomers of formula (I) have been found to be agonists and partial agonists at 5-HT$_1$-like receptors. Nomenclature of 5-HT receptors is constantly evolving. At least four subtypes of the 5-HT$_1$ receptor family have been described, namely 5-HT$_{1a}$, 5-HT$_{1b}$, 5-HT$_{1c}$ and 5-HT$_{1d}$. Functional contractile 5-HT$_1$-like receptors have been identified in the dog saphenous vein and in cerebral (basilar) arteries of various species including rabbit and human. It is now believed that the functional 5-HT$_1$-like receptor correlates with the 5-HT$_{1d}$ binding site (A. A. Parsons, TIPS, Aug. 1991, Vol 12).

Enantiomers of formula (I) are expected to have utility in the treatment and/or prophylaxis of migraine, with and without aura, tension headache, cluster headache and othe forms of cephalic pain and trigeminal neuralgias.

The invention therefore further provides the use of an enantiomer of formula (I) or a physiologically acceptable salt thereof in the manufacture of a medicament for the treatment of a condition where a 5-HT$_1$-like agonist is indicated, in particular the treatment or prophylaxis of migraine.

The invention also provides a method of treatment of a condition wherein a 5-HT$_1$-like agonist is indicated, in particular migraine, which comprises administering to a subject in need thereof an effective amount of an enantiomer of formula (I) or a physiologically acceptable salt thereof.

For use in medicine, a compound of the present invention will usually be administered as a standard pharmaceutical composition. The present invention therefore provides in a further aspect pharmaceutical compositions comprising an enantiomer of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

BIOLOGICAL TEST METHODS

5-HT$_1$-like Receptor Screen

RABBIT BASILAR ARTERY

Experiments were performed in intracranial arteries from rabbit isolated basilar artery in a similar method to that described previously (Parsons and Whalley, 1989, Eur J Pharmacol 174, 189–196.)

In brief, rabbits were killed by overdose with anaesthetic (sodium pentobarbitone). The whole brain was quickly removed and immersed in ice cold modified Kreb's solution and the basilar artery removed with the aid of a dissecting microscope. The Krebs solution was of the following composition (mM) Na$^+$ (120); K$^+$ (5); Ca$^{2+}$ (2.25)Mg$^{2+}$ (0.5); Cl$^-$ (98.5); SO$_4^{2-}$ (1); ETDA (0.04), equilibrated with 95% O$_2$/5% CO$_2$. The endothelium was removed by a gentle rubbing of the lumen with a fine metal wire. Arteries were then cut into ring segments (ca 4–5 mm wide) and set up for recording of isometric tension in 50 ml tissue baths in modified Krebs solution with the additional supplement of (mM); Na$^{2+}$ (20); fumarate (10); pyruvate (5); L-glutamate (5) and glucose (10). The arteries were then placed under a resting force of 3–4 mN maintained at 37° C. and the solution bubbled with 95% O$_2$/5% CO$_2$.

After tests for initial reactivity with 90 mM KCl depolarising solution and for lack of acetylcholine-induced relaxation of 5-HT (10 mM) precontraction, cumulative concentration-effect curves (2 nM–60 mM) to 5-HT were constructed in the presence of ascorbate 200 mM, cocaine 6 mM, indomethacin 2.8 mM, ketanserin 1 mM and prazosin 1 mM.

Following a 45–60 min wash period, cumulative concentration-effect curves to the test compounds or 5-HT (as a time match control) were constructed in the presence of ascorbate, indomethacin, cocaine, ketanserin and prazosin.

Test Compounds:
R-(+)-6-carboxamido-3-N-methylamino-1,2,3,4-tetrahydrocarbazole; (compound A)
S-(−)-6-carboxamido-3-N-methylamino-1,2,3,4-tetrahydrocarbazole; (compound B)
R-(+)-6-carboxamido-3-N-ethylamino-1,2,3,4-tetrahydrocarbazole; (compound C)
S-(−)-6-carboxamido-3-N-ethylamino-1,2,3,4-tetrahydrocarbazole. (compound D)

| Results | EC$_{50}$ |
| --- | --- |
| Compound A | 0.03 µM |
| Compound B | >2 µM |
| Compound C | 0.16 µM |
| Compound D | 2.1 µM |

Pharmaceutical Formulations

The following represent typical pharmaceutical formulations according to the present invention, which may be prepared using standard methods.

| IV Infusion | |
| --- | --- |
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.
Solvent: Typically water but may also include cyclodextrins (1–100 mg) and co-solvents such as propylene glycol, polyethylene glycol and alcohol.

| Tablet | |
| --- | --- |
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins
Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension | |
| --- | --- |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin

PREPARATION 1

(±)-3-Amino-6-carboxamido-1,2,3,4-tetrahydrocarbazole

4-Carboxamidophenylhydrazine hydrochloride (2.87 g) and 4-phthalimidocyclohexanone (3.00 g) were mixed in acetic acid and the mixture was heated under reflux for 2 hr.

After cooling, the mixture was neutralized using aq. potassium carbonate solution, and the yellow solid thus obtained was filtered, washed with water, and dried. Purification by column chromatography (SiO$_2$; CHCl$_3$/CH$_3$OH) gave 6-carboxamido-3-phthalimido-1,2,3,4-tetrahydrocarbazole (2.8 g).

The above product (1.0 g) was suspended in ethanol (10 ml) and hydrazine hydrate (5 ml) was added. A clear solution was obtained, and the mixture was left to stir overnight, to yield a precipitate. The whole mixture was evaporated to dryness, washed with aq. K$_2$CO$_3$ solution, and water, to leave the title compound 3-amino-6-carboxamido-1,2,3,4-tetrahydrocarbazole (0.44 g), as the monohydrate, mp. 146°–148° C.

$^1$H NMR [250 MHz, DMSO-d$^6$]δ 1.49–1.77 (1H,m), 1.83–2.03 (1H,m), 2.17–2.40 (1H,m), 2.62–2.80 (2H,m), 2.90 (1H,dd), 1 signal obscured by H$_2$O at ca. 3.1, 7.03 (1H,brd.s), 7.18 (1H,d), 7.58 (1H,d), 7.83 (1H,brd.s), 7.98 (1H,s).

PREPARATION 2

(+)- and (−)-2-Amino-6-carboxamido-1,2,3,4-tetrahydrocarbazole hydrochloride

Method 1

(±)-3-t-Butyloxycarbonylamino-6-carboxamido-1,2,3,4-tetrahydrocarbazole was separated into its enantiomers using chiral HPLC: (chiralcel OD 4.6 mm column, eluting with hexane/ethanol 85:15). The (+)-enantiomer was collected first and had mp=150°–152° C. and $[\alpha]_D^{25}$=+70.1 (in methanol, 0.41% w/v). The (−)-enantiomer had mp=150°–152° C. and $[\alpha]_D^{25}$=−79.4 (in methanol, 0.40% w/v). The (+)-enantiomer was converted to the parent amine hydrochloride by treating with HCl gas in dioxane, to furnish the (+)-enantiomer of 3-amino-6-carboxamido-1,2,3,4-tetrahydrocarbazole hydrochloride, mp=248°–251° C., $[\alpha]_D^{25}$=+26.2 (in methanol, 0.50% w/v). The (−)-enantiomer of 3-t-butyloxycarbonylamino-6-carboxamido-1,2,3,4-tetrahydrocarbazole was similarly converted into the (−)-enantiomer of 3-amino-6-carboxamido-1,2,3,4-tetrahydrocarbazole hydrochloride, mp=248°–251° C., $[\alpha]_D^{25}$=−28.6 (in methanol, 0.50% w/v).

Method 2

(±)-3-amino-6-carboxamido-1,2,3,4-tetrahydrocarbazole was treated with one equivalent of 2,3:4,6-di-O-isopropylidene-2-keto-L-gulonic acid in methanol to give the salt of the (+)-enantiomer, in 38% yield (with respect to racemate) and 84% enantiomeric excess (ee). This material was recrystallized twice from methanol to give the salt of the (+)-enantiomer in 25% overall yield (with respect to racemate), and >98% ee. This product was converted to the hydrochloride salt first by treatment with aqueous alkali, and the precipitated free base treated with 2M aq. HCl in ethanol, to give (+)-3-amino-6-carboxamido-1,2,3,4-tetrahydrocarbazole hydrochloride.

PREPARATION 3

(±)-6-Carboxamido-3-N-methylamino-1,2,3,4-tetrahydrocarbazole hydrochloride

4-Cyanophenyl hydrazine hydrochloride (20.2 g) and 4-benzoyloxycyclohexanone (25.9 g) were dissolved in glacial acetic acid (400 ml) and the mixture was heated under reflux for 1.5 hr. After allowing to cool, the mixture was filtered, and the filtrate was evaporated to dryness, and neutralized with aqueous sodium bicarbonate solution to give a solid precipitate, which was purified by chromatography (SiO$_2$; hexane/ethyl acetate) to give 3-benzoyloxy-6-cyano-1,2,3,4-tetrahydrocarbazole (18 g). This product (11.6 g) was suspended in ethanol (230 ml) and treated with 2.5% aqueous potassium hydroxide solution (120 ml), and heated under reflux for 1 hr. The cooled mixture was neutralized with glacial acetic acid and evaporated to a solid residue, which was washed with water, and dried to give 3-hydroxy-6-cyano-1,2,3,4-tetrahydrocarbazole (6.6 g).

The above product (3.57 g) was dissolved in dry pyridine (35 ml) and treated with tosyl chloride (3.51 g) in dry pyridine (35 ml), and the mixture was stirred at 100° C. for 2 hr. After cooling, the solution was poured into water (500 ml), extracted with ethyl acetate, and the latter extract was washed with 2M HCl, dried (MgSO$_4$) and evaporated to dryness. Purification by chromatography (SiO$_2$; hexane/ethyl acetate) gave 3-tosyloxy-6-cyano-1,2,3,4-tetrahydrocarbazole (0.53 g).

This product (0.40 g) was dissolved in 33% methylamine in alcohol (25 ml) and heated at 100° C. in a sealed steel vessel for 1.5 hr. After cooling, the mixture was evaporated to dryness and purified by chromatography (SiO$_2$; chloroform/methanol) to give 3-methylamino-6-cyano-1,2,3,4-tetrahydrocarbazole (0.13 g).

The above product (0.12 g) was dissolved in THF (10 ml) and reacted with di-tert-butyl dicarbonate (0.36 g) in THF (3 ml) at room temperature overnight. The reaction mixture was evaporated to dryness, partitioned between 2M sodium bicarbonate solution and ethyl acetate, and the organic extract dried and evaporated to give a white solid. This was triturated with ether/hexane to give 3-t-butyloxycarbonylmethylamino-6-cyano-1,2,3,4-tetrahydrocarbazole (0.14 g).

This product (0.14 g) was dissolved in methanol (15 ml) and treated with a mixture of 20% aqueous sodium hydroxide (0.20 ml) and 30% hydrogen peroxide (0.20 ml), and the whole mixture was stirred at room temperature overnight. Sodium metabisulphite (38 mg) was added, and the solution was evaporated to dryness, and chromatographed (SiO$_2$; chloroform/10% NH$_4$OH in methanol) to give 3-methylamino-6-carboxamido-1,2,3,4,-tetrahydrocarbazole (0.12 g). The above compound (0.11 g) was dissolved in methanol (10 ml), and treated with 3M hydrochloric acid at room temperature. The mixture was evaporated to dryness, azeotroping with ethanol to give a solid, which was recrystallized from methanol/ether to give the title compound, mp 327°–328° C. (80 mg).

1H NMR [250 MHz, MeOH-d$^4$] d 1.98–2.20 (1H,m), 2.29–2.49 (1H,m), 2.75–2.90 (5H, s+m), 2.90–3.09 (2H, m), 3.52–3.69 (1H, m), 7.31 (1H, d), 7.63 (1H, d), 8.05 (1H, s).

PREPARATION 4

(±)-6-Carboxamido-3-N-ethylamino-1,2,3,4-tetrahydrocarbazole oxalate 1,4-Cyclohexanedione mono-2',2'-dimethyl trimethylene ketal (2.00 g) was mixed with anhydrous ethylamine (10.0 g) and benzene (10 ml), and the mixture was cooled to 5° C. A solution of titanium tetrachloride (0.95 g) in benzene (10 ml) was added, dropwise, then the mixture was stirred at room temperature for 1 hr. The mixture was filtered, and evaporated to dryness to give an oil, which was dissolved in ethanol (30 ml). To this solution was added palladium-on-carbon catalyst (100 mg), and the mixture was hydrogenated at 50 psi pressure overnight. The catalyst was filtered off and the ethanol evaporated to leave 4-ethylamino-cyclohexanone 2',2'-dimethyl trimethylene ketal as an oil (2.0 g).

This compound (0.80 g) was dissolved in formic acid (20 ml) and the solution was heated to 90° C. for 1 hr. Formic acid was evaporated, and the residue was partitioned between chloroform and 1M hydrochloric acid. The aqueous layer was evaporated to dryness to give 4-ethylaminocyclohexanone (0.40 g).

A mixture of the above product (0.40 g) and 4-carboxamidophenyl hydrazine hydrochloride (0.60 g) in glacial acetic acid (20 ml) was heated under reflux for 1 hr. The acid was evaporated in vacuo to an oil, which was purified by chromatography ($SiO_2$; $CHCl_3$/10% $NH_3$ in MeOH) to give an oil (0.50 g). Part of this product (150 mg) was dissolved in methanol and treated with oxalic acid. The solution was treated with ether to give the title compound as a crystalline solid, mp 165°–170° C. (100 mg).

1H NMR [250 MHz, DMSO-$d^6$]δ 1.25 (3H, t), 1.81–2.05 (1H, m), 2.20–2.38 (1H, m), 2.61–2.79 (1H, m), 2.79–2.94 (2H, m), 2.98–3.28 (3H, dd+s), 3.41–3.60 (1H, m), 7.08 (1H, brd. s), 7.28 (1H, d), 7.60 (1H, d), 7.82 (1H, brd. s), 8.00 (1H, s), 11.12 (1H, s).

PREPARATION 5

(±)-6-Carboxamido-3-N-methylamino-1,2,3,4-tetrahydrocarbazole

A solution of (±)-6-carboxamido-3-N-methylamino-1,2, 3,4-tetrahydrocarbazole hydrochloride salt (6.0 g) in water (60 ml) at 68° C. was basified to pH 10.5 with 5M aqueous sodium hydroxide. The resultant mixture was extracted with butan-1-ol (30 ml, 15 ml). These extracts were combined and evaporated to give the title compound as a dark oil (6.96 g) containing ca. 46% w/w butan-1-ol.

1H NMR[400 MHz,$d^6$-DMSO]δ 1.40–2.00 (1H,br), 1.62 (1H,m), 2.06 (1H,m), 2.33 (1H,m) 2.39 (3H,s), 2.77 (3H,m), 2.97 (1H,dd), 7.02 (1H,s), 7.24 (1H,d), 7.59 (1H,dd), 7.80 (1H,s), 7.99 (1H,d), 10.93 (1H,s)+peaks due to butan-1-ol.

PREPARATION 6

4-Methylaminocyclohexanone (2',2'-dimethyltrimethylene) ketal hydrochloride 1,4-Cyclohexanedione (mono-2'2'-dimethyltrimethylene) ketal (50 g) was dissolved in dry toluene (500 ml) in a flask fitted with a dry ice trap and flushed with nitrogen with stirring. Methylamine (47.0 g) was then added dropwise to the reaction mixture, at 20° C. slowly to allow dissolution in the toluene. Molecular sieves (32.0 g) were then added and the reaction mixture stirred at 20° C. under an air lock. The reaction was complete after ca. 4 h (>97%). The sieves were then filtered off and the clear amber filtrate evaporated to a volume of 160 ml. The concentrated solution of iminoketal was diluted with ethanol (340 ml) and degassed with argon. Palladium catalyst (palladium on charcoal, 3.55 g) was added and the mixture hydrogenated at atmospheric pressure and 20° C. for 24 h. When hydrogen uptake was complete the reaction mixture was filtered through Celite and the Celite bed washed with a little ethanol (2×25 ml). The solvent was then removed under reduced pressure to give the ketal amine as an amber oil, (49.12 g, 92%).

The ketal amine (80 g, 0.375 Mol) was dissolved in isopropyl ether with stirring. A solution of HCl in isopropyl ether (prepared by bubbling a known weight of gas into a known volume of solvent) was added dropwise causing the formation of an immediate white precipitate, which became very thick as the addition was completed. The thick suspension was stirred for a further 30 minutes, filtered off, and the product washed with a little fresh isopropyl ether and then dried under vacuum to give the title compound as a white, free flowing powder (84.01 g).

1H NMR: [270 MHz, $CDCl_3$]δ 9.51 (2H,bs), 3.48 (4H,d), 3.00 (1H,m), 2.73 (3H,t), 2.32 (2H,d), 2.15 (2H,d), 1.85, (2H,dq), 1.41 (2H,dt), 0.96 (6H,s).

PREPARATION 7

(±)-6-Carboxamide-3-methylamino-1,2,3,4-tetrahydrocarbazole hydrochloride

4-Aminobenzamide (3.0 g) was dissolved in 5N HCl (20 ml) cooled to −5° to 0° C. with stirring and the mixture further cooled to around −15° C. Sodium nitrite (1.98 g) in water (4.4 ml) was added dropwise with stirring at such a rate that the temperature was maintained at between −10° to −15° C. The mixture was then stirred at around −8° C. for 30 min. Ice cold water (40 ml) was then added followed by solid sodium dithionite (7.7 g) in a single portion, the means of cooling removed and the mixture stirred at around 15° C. for 30 min. To the resulting yellow suspension was added conc. HCl (30 ml) followed by 4-methylaminocyclohexanone (2'2'-dimethyltrimethylene) ketal hydrochloride (5.488 g) and the mixture heated to around 70° C., not allowing the reaction temperature to rise above 75° C. After ca. 2 h, the reaction mixture was cooled to 20° C. and the dark solution then carefully neutralised with caustic (aq., 40%) to pH 10 maintaining the temperature between 15°–20° C., whereupon a thick precipitate formed to give the title compound. The reaction mixture was then left to stir overnight and the precipitate filtered off and dried (3.88 g, 63%).

$^1$H nmr [250 MHz, $d_6$DMSO]δ=11.21 (1H,s), 8.06 (1H,s), 7.89 (1H,bs), 7.63 (1H,d), 7.28 (1H,d), 7.10 (1H,bs), 3.50–3.15 (2H,m), 2.95–2.70 (3H,m), 2.62 (3H,s), 2.33 (1H,m), 1.97 (1H,m).

PREPARATION 8

4-Methylaminocyclohexanone (2',2'-dimethyltrimethylene) ketal hydrochloride 1,4-Cyclohexanedione mono-2,2-dimethyltrimethylene ketal (20.0 g, 0.101 mol) was dissolved in ethanol (200 ml) containing methylamine (8.0 g, 0.258 mol). The resultant solution was hydrogenated at 30 psi over 10% Pd/C catalyst (2.0 g) for 4 hrs at room temperature. The reaction mixture was filtered through a celite pad and the filtrate evaporated under reduced pressure to give an oil (21.4 g).

The oil was dissolved in tetrahydrofuran (210 ml) and the resultant solution cooled in an ice/water bath while conc.HCl (10.5 ml) was added to the stirred solution in two portions such that the temperature did not rise above 15° C. and then filtered. The solid was washed with THF (50 ml) and air dried overnight to give the title compound (22.80 g). mp 245.1° C. (EtOH).

$^1$H nmr (250 MHz, $d_6$DMSO)δ 0.9 (s,6H), 1.3(q,2H), 1.45 (q,2H), 1.9 (brd,2H), 2.25 (brd,2H), 2.5 (s,3H), 3.0 (m,1H), 3.5 (d,4H).

EXAMPLE 1

(+) and (−)-6-Carboxamido-3-N-methylamino-1,2,3,4-tetrahydrocarbazole hydrochloride (a) To a stirred solution of (±)-6-carboxamido-3-N-methylamino-1,2,3,4-tetrahydrocarbazole hydrochloride (0.3 g) in propan-2-ol/saturated aqueous potassium hydrogen carbonate (20:1 21 ml), di-tert-butyl dicarbonate (0.425 g) was added and stirring continued for 1 hour. The mixture was diluted with ethyl acetate (50 ml) washed with waster (2×20 ml), dried (MgSO$_4$) and solvent removed at reduced pressure to give (±) 3-N-tert-butoxycarbonyl-N-methylamino-6-carboxamido-1,2,3,4-tetrahydrocarbazole (0.36 g).

$^1$H NMR (d$_6$-DMSO) δ 1.47(s,9H), 1.84–2.08(m,2H), 2.71–2.94(m,4H), 2.80(s,3H), 4.26(m,1H), 7.02(br.s,1H), 7.25(d,1H), 7.57(d,1H), 7.76(br.s,1H), 7.97(s,1H) and 10.96(s,1H).

(b) The (+) and the (−) enantiomers (±)-3-N-tert-butoxycarbonyl-N-methylamino-6-carboxamido-1,2,3,4-tetrahydrocarbazole (0.3 g) were separated by chiral HPLC: (chiralpak AD 20 mm column, hexane:ethanol 9:1 eluant).

Treatment of the first eluting enantiomer (0.02 g) with 3N aqueous hydrochloric acid/methanol 1:1 (4 ml) for 16 hours, filtration and removal of solvent gave, after recrystallisation from methanol/diethyl ether, the (+) enantiomer of the title compound (0.009 g) m.p. 219°–225° C., $[α]_D^{25° C.}=+25.4$ (methanol 0.063% w/v).

Treatment of the second eluting enantiomer (0.03 g) under similar conditions gave the (−) enantiomer of the title compound (0.02 g), m.p. 219°–225° C. $[α]_D^{25° C.}=-23.3$ (methanol 0.116% w/v).

EXAMPLE 2

(+)-6-Carboxamido-3-N-methylamino-1,2,3,4-tetrahydrocarbazole (a) To a solution of (±)-6-carboxamido-3-N-methylamino-1,2,3,4-tetrahydrocarbazole (0.77 g) in dimethylformamide (70 ml), triethylamine (0.62 g) and benzyl chloroformate (0.47 g) were added. The solution was stirred overnight, further triethylamine (0.27 g) and benzyl chloroformate (0.26 g) added and the mixture stirred for 4 hours. The reaction mixture was poured into water (500 ml), and extracted with ethyl acetate (2×50 ml). The combined extracts were dried (MgSO$_4$) and solvent was removed at reduced pressure. The residue was recrystallised from methanol/water to give (±)-3-N-benzyloxycarbonyl-6-carboxamido-3-N-methylamino-1,2,3,4-tetrahydrocarbazole (0.62 g) m.p.103°–110° C.

(b) The (+) and (−) enantiomers of (±)-3-N-benzyloxycarbonyl-6-carboxamido-3-N-methylamino-1,2,3,4-tetrahydrocarbazole were separated by chiral HPLC (OD column, eluant hexane/ethanol 4:1).

The first eluting enantiomer (0.23 g) m.p. 105°–106° C., $[α]_D^{25° C.}=+157.2$. (ethanol, 0.39% w/v).

The second eluting enantiomer (0.23 g) m.p. 105°–106° C., $[α]_D^{25° C.}=-163.1$ (ethanol, 0.23% w/v).

(c) A solution of (+)-3-N-benzyloxycarbonyl-6-carboxamido-3-N-methylamino-1,2,3,4-tetrahydrocarbazole (0.23 g) in ethanol (20 ml) containing 10% palladium/charcoal (0.23 g) was shaken under a hydrogen atmosphere (50 psi) for 3 hours. Catalyst was removed by filtration and solvent removed at reduced pressure to give the (+) enantiomer of the title compound (free base) as a foam m.p. 98°–102° C., $[α]_D^{25° C.}=+61.2$.

EXAMPLE 3

(+)-6-Carboxamido-3-N-methylamino-1,2,3,4-tetrahydrocarbazole camphorsulphonate

To a solution of (±)-6-carboxamido-3-N-methylamino-1,2,3,4-tetrahydrocarbazole (3 g) in methanol (20 ml), a solution of (1S)-(+)-10-camphorsulphonic acid (2.86 g) in methanol was added. Solvent was removed at reduced pressure and the residue recrystallised ten times to give the (+) enantiomer of the title compound as the camphorsulphonate salt m.p. 177°–180° C. This was treated with 2 equivalents of triethylamine and 10 equivalents of 2,3,4,6-tetra-o-acetyl-beta-D-glucopyranosylisothiocyanate in dimethylformamide at room temperature for 30 minutes. Aliquots of the reaction mixture wre removed from the mixture for HPLC analysis. Analytical HPLC of the 2,3,4,6-tetra-O-acetyl-beta-D-glucopyranosylthiourea derivative (C18 Novapak, eluant methanol/50 mM NaH$_2$PO$_4$ pH 2.9) gave the same retention time as the the same derivative prepared from the (+) enantiomer of Example 1 and showed the material was 99% ee.

EXAMPLE 4

(+)-6-Carboxamido-3-N-methylamino-1,2,3,4-tetrahydrocarbazole succinate (1:1)

(a) Benzaldehyde (10.6 g) was added to a suspension of (+)-3-amino-6-carboxamido-1,2,3,4-tetrahydrocarbazole (12.35 g) in methanol (100 ml). The mixture was stirred for 1 hour, sodium cyanoborohydride (9.3 g) added over 1 hour and the clear solution stirred for 24 hours. The solution was cooled (ice bath) and formaldehyde (37% aqueous methanolic, 9:1 solution, 5.5 ml) added. After 30 minutes stirring at room temperature water (100 ml) was added, stirring continued for 30 minutes followed by extraction with dichloromethane (3×150 ml). The combined organic extracts were washed with water (2×200 ml), dried (Na$_2$SO$_4$), filtered and solvent removed at reduced pressure. The residue was column chromatographed (silica gel, dichloromethane-10% ethanol/dichloromethane) to give 3-N-benzyl-6-carboxamido-3-N-methylamino-1,2,3,4-tetrahydrocarbazole (9.4 g) as a foam. The succinate salt (1:1) was recrystallised from methanol m.p. 175°–182° C.

$^1$H NMR (d$_6$-DMSO)δ 1.81–1.96(m,1H), 2.09–2.21(m, 1H), 2.29(s,3H), 2.44(s,4H), 2.66–3.11(m,5H), 3.76(q,2H), 7.05(br.s1H), 7.22–7.43(m,6H), 7.59(d,1H), 7.79(br. s,1H), 8.03(s,1H), and 10.94(s,1H).

(b) To a solution of 3-N-benzyl-6carboxamido-3-N-methylamino-1,2,3,4-tetrahydrocarbazole (1.0 g) in ethanol (100 ml) containing succinic acid (0.39 g), Pearlmans catalyst (1.0 g) was added and the mixture shaken under an atmosphere of hydrogen at 45 psi and 50° C. for 2 hours. The mixture was filtered (celite pad) and the pad washed thoroughly with ethanol. The combined filtrate and washings were evaporated to dryness, co-evaporated with ethanol (3×100 ml) and recrystallised from methanol to give the title compound [(1:1) succinate salt]. m.p. 148°–155° C.

¹H NMR (d₆-DMSO)δ 1.84(m,1H), 2.15–2.34(m,1H), 2.28(s,4H), 2.57(m,1H), 2.61(s,3H), 2.83(m,2H), 3.13(dd, 1H), 3.29(m,1H), 7.08(br s,1H), 7.26(d,1H), 7.60(dd,1H), 7.82(br s,1H), 8.01(d,1lH) and 11.08(s,1H).

EXAMPLE 5

(+)-6-Carboxamido-3-N-methylamino-1,2,3,4-tetrahydrocarbazole (a) To a solution of (+)-3-amino-6-carboxamido-1,2,3,4-tetrahydrocarbazole (5 g) in pyridine (150 ml), dicyclohexylcarbodiimide (4.13 g) was added followed by carbon disulphide (1.67 g). The solution was stirred for 1 hour, solvent removed at reduced pressure and the residue co-evaporated with toluene (3×100 ml). The residue was recrystallised from methanol to give 6-carboxamido-3-isothiocyanato-1,2,3,4-tetrahydrocarbazole (5.06 g) m.p.245°–248° C.

(b) A solution of 6-carboxamido-3-isothiocyanato-1,2,3,4-tetrahydrocarbazole (0.25 g) in ethanol (40 ml) was treated with sodium borohydride (0.17 g) in one portion and stirred for 18 hours. Acetone (5 ml) was added the mixture stirred for a further 1 hour and solvent removed at reduced pressure. The residue was column chromatographed (basic alumina, 5% methanol/dichloromethane eluant) to give the title compound (0.11 g) having the same physico chemical characteristics as the product of Example 2.

EXAMPLE 6

(+)- and (–)-6-Carboxamido-3-N-ethylamino-1,2,3,4-tetrahydrocarbazole hydrochloride (a) From (±)-6-carboxamido-3-N-ethylamino-1,2,3,4-tetrahydrocarbazole (0.26 g), (±)-3-N-tert butoxycarbonyl-N-ethylamino-6-carboxamido-1,2,3,4-tetrahydrocarbazole (0.27 g) isolated as an oil was prepared according to the procedure of Example 1.

¹H NMR (d₆-DMSO) δ 1.1(t,3H), 1.23(s,9H) 1.92(m,1H), 2.09(m,1H), 2.78–2.92(m,4H), 3.21–3.62(m,2H), 4.21(m, 1H), 7.04(br.s,1H), 7.24(d,1H), 7.58(d,1H), 7.76(br.s,1H), 7.99(s,1H) and 10.99(s,1H).

(b) From (±)-3-N-tert butoxycarbonyl-3-N-ethylamino-1,2,3,4-tetrahydrocarbazole (0.25 g), the (+)- and the (–)-enantiomers of 3-N-tert butoxycarbonyl-3-N-ethylamino-1,2,3,4-tetrahydrocarbazole were prepared by chiral HPLC (chiralcel OD 4.67 mm, eluant hexane/ethanol 92/8).

Treatment of the enantiomer eluting first, (0.06 g) [α]$_D^{25°\ C.}$=+108.2 (ethanol 0.9% w/v) with hydrochloric acid/methanol according to the method of Example 1 gave (+)-6-carboxamido-N-ethylamino-1,2,3,4-tetrahydrocarbazole hydrochloride (0.04 g) m.p. 211°–221° C. [α]$_D^{25°\ C.}$=+37.2 (methanol, 0.12% w/v).

Treatment of the second eluting enantiomer (80 mg) [α]$_D^{25°\ C.}$=–103.5 (ethanol, 0.19% w/v) with hydrochloric acid/methanol according to the method of Example 1 gave (–)-6-carboxamido-3-N-ethylamino-1,2,3,4-tetrahydrocarbazole hydrochloride (0.05 g) m.p. 211°–221° C. after recrystallisation from methanol/diethyl ether [α]$_D^{25°\ C.}$=–33.6 (methanol, 0.11% w/v).

EXAMPLE 7

(+)-6-Carboxamido-3-N-ethylamino-1,2,3,4-tetrahydrocarbazole succinate (1:1)

(a) From (+)-3-amino-6-carboxamido-1,2,3,4-tetrahydrocarbazole (1.15 g), (+)-3-benzyl-N-ethylamino-6-carboxamido-1,2,3,4-tetrahydrocarbazole (1.26 g) was obtained according to the procedure of Example 4 replacing formaldehyde with acetaldehyde (0.44 g). The succinate salt (1:1) was prepared by addition of succinic acid (0.4 g) to the free base (1.08 g) and recrystallisation from propan-2-ol m.p 130°–140° C.

¹H NMR (d₆-DMSO) δ 1.05(t,3H), 1.85(m,1H), 2.10(m, 1H), 2.40(s,4H), 2.58–2.91(m,5H), 3.06(m,1H), 3.77(q,2H), 7.03(br.s,1H), 7.17–7.47(m,5H), 7.58(d,1H), 7.78(br.s,1H), 8.00(s,1H), 10.90(s,1H) and 12.28(br.s2H).

(b) Recrystallisation of (+)-3-N-benzyl-N-ethylamino-6-carboxamido-1,2,3,4-tetrahydrocarbazole succinate (1.36 g), from methanol, according to the procedure of Example 4 gave the title compound (1.04 g) m.p. 165°–167° C.

1H NMR (d6-DMSO) δ 1.19(t,3H), 1.86(m,1H), 2.23(m, 1H), 2.30(s,4H), 2.62(m1H), 2.85(m,2H), 3.02(q,2H), 3.14(m,1H), 3.38(m,1H), 7.08(br.s,1H), 7.26(d,1H), 7.59(d, 1H), 7.80(br.s,1H), 8.00(s,1H) and 11.08(s,1H).

EXAMPLE 8

(+)-6-Carboxamido-3-N-methylamino-1,2,3,4-tetrahydrocarbazole L (+)-tartrate salt (1:1)

To a hot solution of (+)-6-carboxamido-3-N-methylamino-1,2,3,4-tetrahydrocarbazole (0.25 g) in methanol/water (11:1, 24 ml) L (+)-tartaric acid (0.15 g) was added and the solution allowed to stand for 3 hours. The crystalline title compound (0.30 g) was isolated by filtration. m.p. 195°–197° C.

¹H NMR (d₆-DMSO) δ 1.92(m,1H), 2.25(m,1H), 2.67(s, 3H), 2.68(m,1H), 2.84(m,2H), 3.17(dd,1H), 3.43(m,1H), 3.87(s,2H), 7.07(br.s,1H), 7.27(d,1H), 7.61(d,1H), 7.82(br.s, 1H), 8.01(s,1H) and 11.11(s,1H).

EXAMPLE 9

(+)-6-Carboxamido-3-N-methylamino-1,2,3,4-tetrahydrocarbazole D (–)-tartrate salt (1:1)

To a hot solution of (+)-6-carboxamido-3-N-methylamino-1,2,3,4-tetrahydrocarbazole (0.25 g) in methanol (9 ml) D (–)-tartaric acid (0.15 g) was added and the solution allowed to stand for 3 hours. The crystalline title compound (0.32 g) was isolated by filtration m.p. softens above 147° C.

¹H NMR (d₆-DMSO)δ 1.92(m,1H), 2.25(m,1H), 2.67(s, 3H), 2.68(m,1H), 2.84(m,2H), 3.17(dd,1H), 3.43(m,1H), 3.87(s,2H), 7.07(br.s,1H), 7.27(d,1H), 7.61(d,1H), 7.82(br.s, 1H), 8.02(s,1H) and 11.09(s,1H).

EXAMPLE 10

(+)-6-Carboxamido-3-N-methylamino-1,2,3,4-tetrahydrocarbazole hemisuccinate (2:1)

To a hot solution of (+)-6-carboxamido-3-N-methylamino-1,2,3,4-tetrahydrocarbazole (0.30 g) in propan-2-ol was added succinic acid (0.07 g) and the solution allowed to stand for 3 hours. The title compound (0.21 g) was isolated by filtration, m.p. 220°–235° C.

¹H NMR (d₆-DMSO)δ 1.77(m,1H), 2.14(m,1H), 2.26(s, 2H), 2.54(s,3H), 2.55(m,1H), 2.79(m;2H), 3.10(dd,1H), 3.43(m,1H), 7.06(br.s,1H), 7.25(d,1H), 7.59(d,1H), 7.82(br.s,1H), 7.99(s,1H) and 11.01(s,1H).

EXAMPLE 11

(+)-6-Carboxamido-3-N-methylamino-1,2,3,4-tetrahydrocarbazole methanesulphonate

To a hot solution of (+)-6-carboxamido-3-N-methylamino-1,2,3,4-tetrahydrocarbazole (0.30 g) in propan-2-ol/ethyl acetate methanesulphonic acid (0.12 g) was added and the solution allowed to stand for 3 hours. The title compound (0.33 g) was isolated as a gum.

¹H NMR (d₆-DMSO)δ 1.93(m,1H), 2.25(m,1H), 2.35(s, 3H), 2.70(m,4H), 2.86(m,2H), 3.10(dd,1H), 3.50(m,1H), 7.11(br.s,1H), 7.27(d,1H), 7.61(d,1H), 7.82(br.s,1H), 8.02(s, 1H), 8.65(br.s,2H) and 11.12(s,1H).

EXAMPLE 12

(+)-6-Carboxamido-3-N-methylamino-1,2,3,4-tetrahydrocarbazole hydrobromide

Hydrogen bromide gas was passed through a solution of (+)-6-carboxamido-3-N-methylamino-1,2,3,4-tetrahydrocarbazole (0.30 g) in ethanol (50 ml) for 15 seconds. After 30 minutes the title compound (0.03 g) m.p. 205°–208° C. was separated by filtration and washed with ethanol.

¹H NMR (d₆-DMSO) δ 1.94(m,1H), 2.25(m,1H), 2.26(s, 2H), 2.70(m,4H), 2.85(m,2H), 3.17(dd,1H), 7.10(br.s,1H), 7.27(d,1H), 7.61(d,1H), 7.82(br.s,1H), 8.02(s,1H) 8.67(br.s, 2H) and 11.01(s,1H).

EXAMPLE 13 a) (+)-6-Carboxamido-3-N-methylamino-1,2,3,4-tetrahydrocarbazole-R-2-pyrrolidone-5-carboxylic acid salt To a solution of (±)-6-carboxamido-3-N-methylamino-1,2,3,4-tetrahydrocarbazole (6.96 g containing ca. 46% w/w butan-1-ol, prepared as in Preparation 5) in ethanol (50 ml), stirred at ambient temperature, was added a solution of R-2-pyrrolidone-5-carboxylic acid (1.00 g, e.e.>99%) in hot ethanol (33 ml). The resultant mixture was stirred at ambient temperature for 40 h. The crystalline product was filtered off under nitrogen, washed with a small volume of ethanol, then dried in vacuo at 60° C. (Yield=2.63 g).

This product was dissolved in water (2.6 ml), and the solution was then diluted with ethanol (130 ml) and stirred at ambient temperature for 40 h. The crystalline product was filtered off, washed and dried as before. (Yield=1.72 g).

This product was recrystallised from ethanol (90 ml)/water (1.8 ml) as described above to give the title compound (1.44 g; e.e.=>99%).

¹H NMR [250 MHz, d₆-DMSO]δ 1.90 (2H,m), 2.06 (2H,m), 2.19 (2H, m), 2.57 (3H,s), 2.62 (1H,m), 2.82 (2H,m), 3.15 (2H,m), 3.80 (1H,dd), 7.07 (1H,s), 7.26 (1H,d), 7.59 (1H,s), 7.62 (1H,s), 7.84 (1H,s), 8.00 (1H,s), 11.10 (1H,s)+peaks due to ethanol.

b) (+)-6-Carboxamido-3-N-methylamino-1,2,3,4-tetrahydrocarbazole succinate salt, monohydrate A solution of (+)-6-carboxamido-3-N-methylamino-1,2,3,4-tetrahydrocarbazole R-2-pyrrolidone-5-carboxylic acid salt (1.34 g) in water (5.4 ml) was basified to pH 1.32 with 5M aqueous sodium hydroxide. The resultant mixture was extracted with butan-1-ol (5.4 ml). This extract was evaporated to give (+)-6-carboxamido-3-N-methylamino-1,2,3,4-tetrahydrocarbazole as an oil/solid (735 mg) containing ca. 2% w/w butan-1-ol.

A portion of this product (232 mg) was dissolved in ethanol (1.45 ml). This solution was filtered, and added dropwise to a stirred solution of succinic acid (110 mg) in ethanol (1.45 ml)/water (0.48 ml). The mixture was seeded before the addition was complete. Stirring was continued for 30 min at ambient temperature, then 30 min at 0° C. The crystalline product was filtered off, washed with a small volume of ethanol, then dried in vacuo at 60° C. Yield=233 mg.

¹H NMR [250 MHz, d₆-DMSO]δ 1.87 (1H,m), 2.25 (1H,m), 2.29 (4H,s), 2.62 (3H,s), 2.65 (1H,m), 2.83 (2H,m), 3.15 (1H,dd), 3.34 (1H,m), 7.09 (1H,s), 7.27 (1H,d), 7.61 (1H,dd), 7.84 (1H,s), 8.02 (1H,s), 11.10 (1H,s).

We claim:

1. A process for preparing (+)-6-carboxamido-3-methylamino-1,2,3,4-tetrahydrocarbazole or a salt, solvate or hydrate thereof which comprises separation of diastereoisomers of a chiral derivative formed by reaction of (±)-6-carboxamido-3-methylamino-1,2,3,4-tetrahydrocarbazole with R-2-pyrrolidone-5-carboxylic acid, by crystallization, or by chromatography.

* * * * *